(12) United States Patent
Kiehne

(10) Patent No.: US 6,991,215 B2
(45) Date of Patent: Jan. 31, 2006

(54) VALVE FOR USE WITH A SYRINGE AND WHICH PREVENTS BACKFLOW

(75) Inventor: Bruce Leigh Kiehne, Springwood (AU)

(73) Assignee: Occupational & Medical Innovations, Ltd., Slacks Creek (AU)

( * ) Notice: Subject to any disclaimer, the term of this patent is extended or adjusted under 35 U.S.C. 154(b) by 51 days.

(21) Appl. No.: 10/475,530

(22) PCT Filed: Jul. 1, 2002

(86) PCT No.: PCT/AU02/00861

§ 371 (c)(1),
(2), (4) Date: Oct. 30, 2003

(87) PCT Pub. No.: WO03/018105

PCT Pub. Date: Mar. 6, 2003

(65) Prior Publication Data

US 2004/0124388 A1    Jul. 1, 2004

(30) Foreign Application Priority Data

Aug. 23, 2001 (AU) .................. 63598/01
Dec. 12, 2001 (AU) .................. PR9444

(51) Int. Cl.
*F16K 51/00* (2006.01)
*F16L 29/00* (2006.01)
*F16L 37/28* (2006.01)

(52) U.S. Cl. .............. 251/149.6; 604/249; 604/905
(58) Field of Classification Search ............ 251/149.1, 251/149.6, 149.7; 604/249, 905
See application file for complete search history.

(56) References Cited

U.S. PATENT DOCUMENTS

| | | | |
|---|---|---|---|
| 3,965,910 A | 6/1976 | Fischer | |
| 5,147,333 A | 9/1992 | Raines | |
| 5,360,413 A * | 11/1994 | Leason et al. | ............... 604/249 |
| 5,520,665 A | 5/1996 | Fleetwood | |
| 5,699,821 A | 12/1997 | Paradis | |
| 5,730,418 A | 3/1998 | Feith et al. | |
| 6,039,302 A * | 3/2000 | Cote et al. | ............... 251/149.1 |
| 6,245,048 B1 | 6/2001 | Fangrow, Jr. et al. | |
| 6,428,520 B1 | 8/2002 | Lopez et al. | |

FOREIGN PATENT DOCUMENTS

| | | |
|---|---|---|
| AU | 736326 | 7/2001 |
| DE | 33 30 148 A1 | 3/1985 |
| EP | 1 027 901 A2 | 8/2000 |
| WO | WO 98/26835 | 6/1998 |

* cited by examiner

*Primary Examiner*—Edward K. Look
*Assistant Examiner*—John K. Fristoe, Jr.
(74) *Attorney, Agent, or Firm*—Hoffman, Wasson & Gitler, PC

(57) ABSTRACT

A one-way valve assembly can be fitted to the end of a syringe to allow fluid to flow from the syringe and into a body cavity but to prevent backflow. The valve assembly is opened by insertion of the luer tip of the syringe into the assembly inlet. The valve has an internal elastic member that forms a variable volume internal chamber. This chamber expands upon insertion of the luer tip into the inlet and shrinks when the luer tip is removed from the assembly. The shrinking action creates a positive pressure in the valve assembly to prevent backflow.

14 Claims, 5 Drawing Sheets

VALVE FOR USE WITH A SYRINGE AND WHICH PREVENTS BACKFLOW

FIELD OF THE INVENTION

This invention is directed to a valve that can be attached to a catheter, a needle or any other type of injecting device and that has a particular configuration to prevent backflow. The invention is particularly directed to a needle free access valve for use in a needle free intravenous access system.

BACKGROUND ART

A needle free access valve is one where the valve can be opened using a needleless syringe. A needleless syringe is a syringe where the needle has been removed such that the front of the syringe has only the luer taper or luer lock. Such valves are known but suffer from a number of disadvantages.

A typical known valve has a body composed of two cylindrical containers. One container has a tubular opening into which the luer taper can be pressed. The other container has a tubular opening filled with a luer lock that allows the valve to be attached to various medical devices. Fluid flows through the luer taper upon depression of the syringe plunger and flows through the valve. The valve has a circular valve disk that can be forced open by the pressure of the fluid. When the fluid pressure stops, the valve returns to its closed position. This type of arrangement is entirely conventional. One disadvantage with this arrangement is that high levels of fluid flow can often not be obtained due to the design of the valve. That is, the valve itself is solid and fluid can flow only about the edge of the valve when the valve is opened. Another disadvantage is the lack of sterilisation around the inlet part of the valve.

A serious disadvantage with many existing one-way valves is that fluid can flow back into the valve from the body cavity or the body in which the needle etc has penetrated. This results in contamination, and a potential health hazard. Most valves are provided with some form of spring or bias to naturally bias the valve back into the closed position. Therefore, there would be a great advantage if it was possible to provide a one-way valve (for instance a needle free access valve) where there is little or no likelihood of backflow occurring upon removal or retraction of the syringe (or other device) to which the valve is attached.

Other disadvantages with conventional valves are the production costs, the relatively large number of components making up the valve, the difficulty in mass production of the valve.

OBJECT OF THE INVENTION

It is an object of the invention to provide a valve assembly for use in the medical field and which can reduce or entirely prevent the occurrence of backflow from the body cavity etc back into the valve assembly.

It is further object of the invention to provide a valve assembly that may at least partially overcome the above-mentioned disadvantages or provide the public with a useful or commercial choice.

In one form, the invention resides in a valve assembly that comprises:
1. An inlet and an outlet,
2. A flow pathway that extends through the valve assembly from the inlet to the outlet,
3. A plunger that is positioned in the flow pathway and which can move between a forward open position where fluid can flow from the inlet to the outlet, and a retracted closed position where fluid is prevented from flowing from the inlet to the outlet, the plunger having a forward portion,
4. An at least partially elastic sock that has an outer end fixed to the valve assembly, and an inner portion which engages with the plunger such that reciprocation of the plunger from the retracted position to the forward position causes at least part of the sock to stretch, and
5. A variable volume chamber having walls defined by the plunger and the sock, the chamber forming part of the flow pathway, the chamber having smaller or nil volume when the plunger is in the retracted position, and a larger volume when the plunger is in the extended position, whereby upon retraction of the plunger, the variable volume chamber reduces in volume which results in a pumping action to pump fluid through the fluid pathway towards the outlet, thereby reducing or preventing backflow.

With this arrangement, the apparatus can be attached to a syringe (or other device), and a needle, catheter or other body-injecting device can be attached to the apparatus. The contents of the syringe can then be passed through the apparatus and into the body by depressing the plunger into the forward (open) position. As the plunger moves towards the forward position, it stretches at least part of the sock and the variable volume chamber adopts the larger volume. However once the syringe is removed, or retracted, the sock retracts to its initial position, causing the plunger to be pushed back into the closed position and at the same time contracting the variable volume chamber. The contraction causes a positive pressure inside the apparatus that means that backflow does not occur. Indeed, it is found that the positive pressure is sufficient to at least partially "pump" any residual fluid in the apparatus through the outlet upon retraction of the plunger. This is in contrast to known devices where retraction of the plunger or closure of the valve often allows backflow of fluid through the outlet and into the valve apparatus.

The valve assembly may have an outer body formed in two parts that are attached together. The two parts may comprise a top part, and a base part. The top part is substantially hollow and suitably contains an outer passageway of smaller diameter or cross-section, and an inner passageway of larger diameter or cross-section, the inner passageway forming part of an internal chamber. The outer passageway may contain longitudinal slots or recesses that comprise fluid ports the reason for which will be described in greater detail below.

The base part may be substantially hollow and may contain a outer passageway of smaller diameter or cross-section, and an inner passageway of larger cross-section or diameter and which forms-part of the internal chamber that is also defined by the top part. Thus, when the two parts are attached, there is provided a substantially central internal chamber. The outer passageway of the base part may be surrounded by attachments to allow the outlet to attach to a needle etc.

The apparatus has a flow pathway that extends through the valve assembly from the inlet to the outlet, and typically through the central internal chamber described above.

The apparatus has a plunger. The plunger is moveable between a forward open position where the plunger moves more towards the outlet, and a retracted closed position where the plunger is more towards the inlet. The plunger typically slides or reciprocates between the two positions.

The plunger has a forward portion which is typically a projecting nose portion. Suitably, the plunger also has a rear body portion. The nose portion and the body portion may be formed integrally. The plunger suitably has a fluid flow pathway extending at least partially therethrough. The fluid flow pathway may comprise an internal flow passageway extending through the nose portion which means that the nose portion may have an open outer end. Suitably, the internal flow passageway includes a transverse through bore in the rear body portion such that fluid can pass through the through bore and through the flow passageway that extends through the nose portion.

The rear body portion of the plunger is typically configured and dimensioned to substantially fill the outer passageway in the top part of the valve assembly. Suitably, the rear body portion has an end face that is substantially flush with the end of the top part of the valve assembly that can make cleaning of this area quite easy. The rear body portion typically has a sealing face extending about the rear body adjacent the end face and which seals with the internal wall of the outer passageway.

The plunger may an engagement means to engage with the elastic sock. The engagement means may comprise an annular step or shoulder portion on the plunger and which can catch against or engage with the elastic sock upon forward movement of the plunger. Alternatively, the plunger can push against the sock.

The apparatus has an at least partially elastic sock. The sock may be formed of a rubbery elastic material having a good memory. In one form of the invention, the sock may be formed as a separate component. The elastic sock may comprise a substantially circular base portion, and an extending tubular wall portion. The base portion and the wall portion may be formed integrally. The wall portion may extend substantially about the nose portion of the plunger. The base portion may have a peripheral edge that is held against movement in the valve assembly. Suitably, the peripheral edge also comprises a sealing edge. Preferably, the base portion is elastic and can therefore be stretched upon forward movement of the plunger. Preferably, the tubular wall portion is compressible or is otherwise configured to allow it to be shortened in length, for instance by allowing the wall portion to buckle in a controlled manner. The wall portion may be provided with circumferential recesses that provide zones to allow a controlled buckling of the wall portion. The end of the tubular wall portion may be provided with a sealing lip or a sealing bead that seals against the base portion of the valve assembly.

Alternatively, the sock may have a substantial disklike configuration without a tubular wall portion. In this embodiment, the sock may have an outer peripheral edge that is attached to the valve assembly in a manner similar to that described above. The sock may have an internal opening, which is typically a central opening and through which part of the plunger can pass, which is typically a nose portion of the plunger. If desired, the plunger may be provided with an annular recess to capture the wall of the internal opening. With this arrangement, the plunger may be provided with seals.

BRIEF DESCRIPTION OF THE DRAWINGS

Embodiments of the invention will be described with reference to the following drawings in which.

BEST MODE

Figure 1:
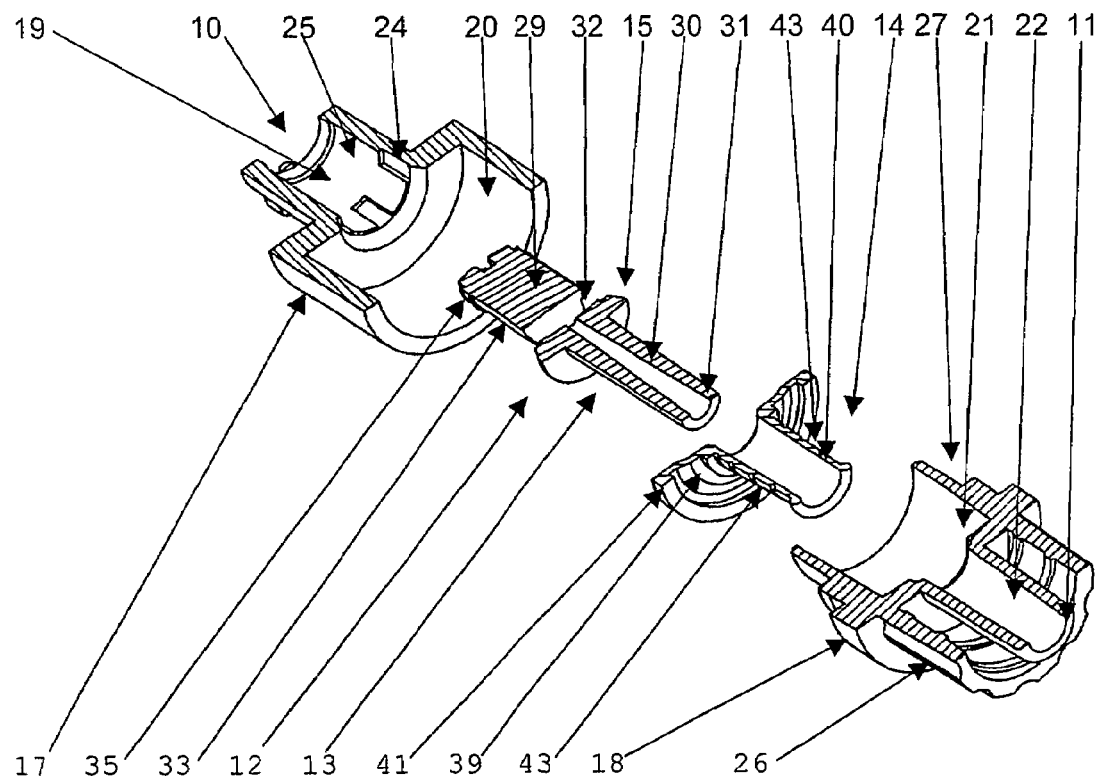
FIG. 1. Illustrates an exploded section view of the various components of the valve apparatus.
Figure 2:
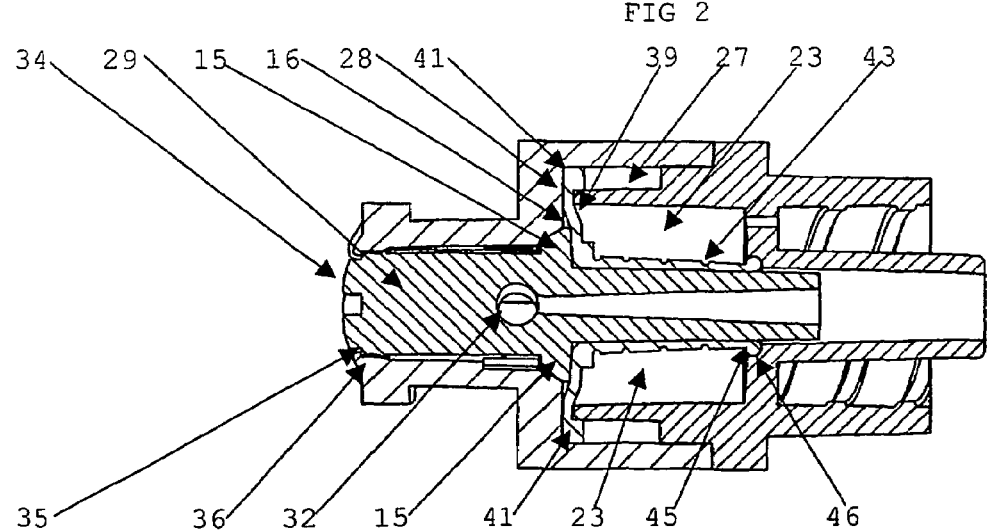
FIG. 2. Illustrates the valve in the closed position with the plunger in the retracted position.
Figure 3:
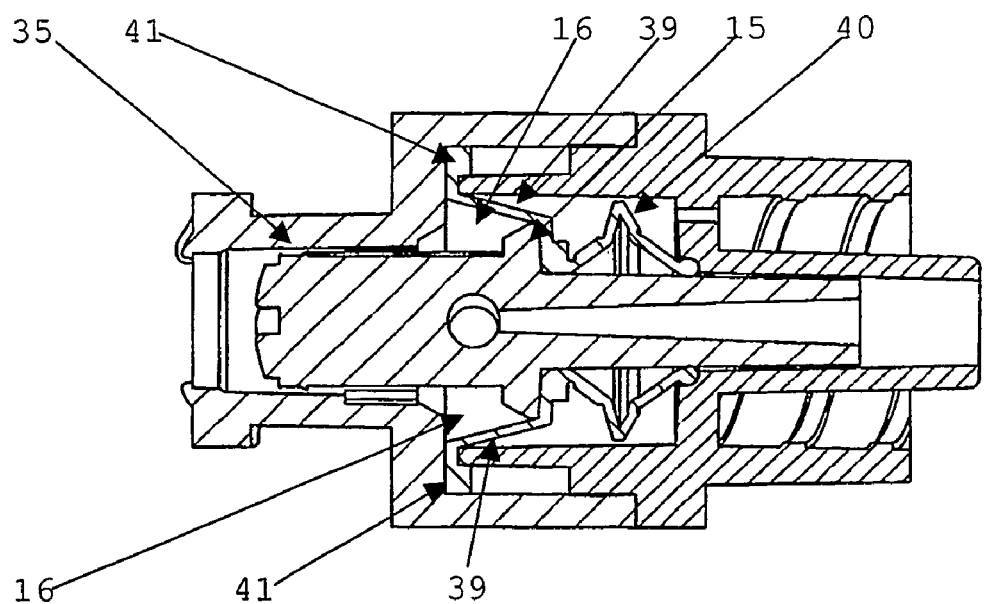
FIG. 3. Illustrates the valve in the partially open position with the plunger moving to the forward position.

Referring to the drawings, and initially to FIG. 1, there is illustrated a valve assembly which comprises an inlet 10 and an outlet 11, a flow pathway that extends through the valve assembly from inlet 10 to outlet 11, a plunger 12 that is positioned in the flow pathway and which can reciprocate between a forward open position illustrated in FIG. 3, and a retracted closed position illustrated in FIG. 2, the plunger having an elongate forward nose portion 13, an elastic sock 14 which is adapted to extend at least partially about the nose portion 13 of plunger 12, engagement means 15 to engage the plunger to the sock, and a variable volume chamber 16 best illustrated in FIG. 3 (where the chamber is of maximum volume), but also just visible in FIG. 2 (where the chamber is of minimal and almost having a zero volume).

Referring to the parts in greater detail, the valve assembly in the embodiment comprises an outer body that is formed of two parts that are attached together, the two parts being a top part 17 and a base part 18. These parts are formed of plastic material and are joined together by any suitable method. Top part 17 is best illustrated in FIG. 1 and is substantially hollow. Top part 17 comprises an outer passageway 19 which is circular and which has a smaller diameter, and an inner passageway 20 which is also circular and which has a substantially larger diameter. Similarly, base part 18 has an inner passageway 21 that has a substantially larger diameter than outer passageway 22. When the two parts are joined as illustrated in FIG. 2 and FIG. 3, the two larger diameter passageways together form an internal chamber 23. Outer passageway 22 terminates in outlet 11, while outer passageway 19 terminates in inlet 10.

The outer passageway 19 in top part 17 contains a plurality of longitudinal open ended fluid ports 24. Ports 24 comprise recesses in the wall of outer passageway 19 and are open ended which means that the ports communicate with chamber 16. The ports 24 do not extend entirely along the wall of passageway 19. Rather, the ports terminate partway along the wall such that a smooth wall portion 25 extends between the end of ports 24 and inlet 10. The reason for this will be described in greater detail below.

Base part 18 contains a standard luer lock fitting 26 which extends about passageway 22 and which functions to allow a needle etc to be attached to this part of the assembly. Of course, other types of attachments can also be used.

Inner passageway 21 has a diameter that is smaller than inner passageway 20. Thus, the wall 27 of inner passageway 21 passes into inner passageway 20 this being best illustrated in FIG. 2. Moreover, wall 27 has a length that results in the wall 27 being spaced somewhat from wall 28 of top part 17 (see FIG. 2). This spacing facilitates the attachment of the elastic sock that will be described in greater detail below.

Plunger 12 is formed of plastic material and comprises a unitary body. The plunger has a particular configuration that provides a nose portion 13, and a rear body portion 29. Nose portion 13 is slightly tapered and has a through passageway 30 which passes through an open outer end 31 and functions to allow fluid to flow through the valve assembly. Body portion 29 is provided with a transverse through bore 32 through which fluid can pass. Body portion 29 has a substantially cylindrical outer wall provided with a sealing area or collar 35. This is why the fluid ports 24 in end wall 25 terminate short of inlet 10 to also provide a smooth area which functions as a sealing zone 36. Thus, when the plunger is in the closed position illustrated in FIG. 2, the sealing collar 35 seals against the sealing zone 36 to provide seal against fluid flow.

Figure 4:
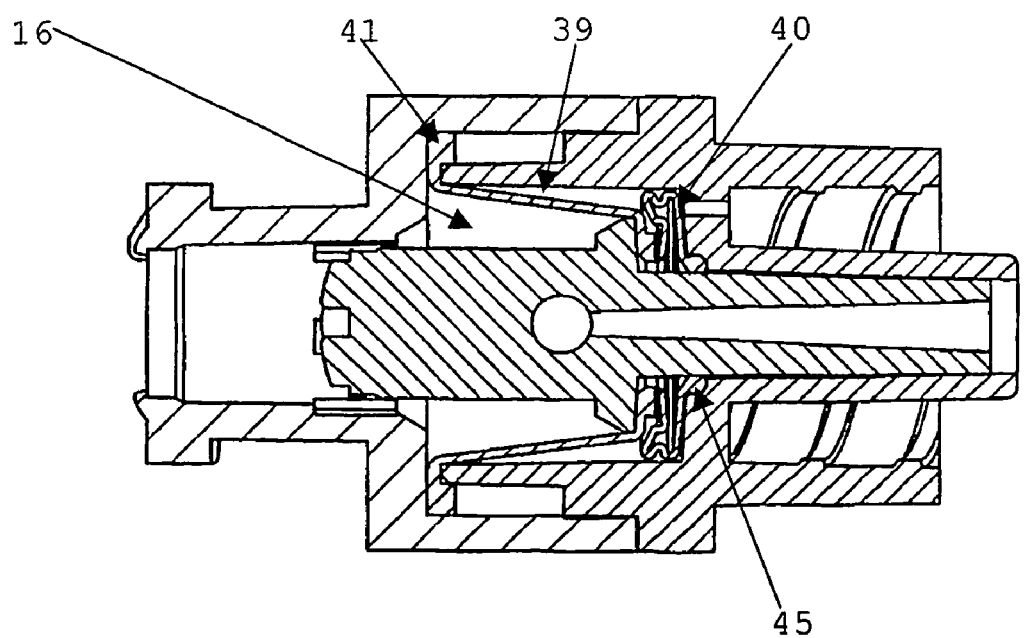
FIG. 4. Illustrates the valve in the fully open position.

When plunger 12 is pushed forwardly from the position illustrated in FIG. 2 to the position illustrated in FIGS. 3 and 4, the plunger only moves by a few mm, but this movement is sufficient to move collar 35 away from sealing zone 36 and into the area of the flow ports 24 and to allow fluid to pass along the outside wall of body portion 29, through the fluid ports 24, through bore 32 through passageway 30 and through outlet 11. Conversely, when the plunger is retracted from the position illustrated in FIG. 3 to the position illustrated in FIG. 2 the plunger again seals against passage of fluid from inlet 10 through outlet 11.

Fluid only flows when the flow ports 24 are opened by collar 35 moving past the outer most edge of the flow ports. At all other times a seal is maintained between the internal wall 25 and collar 35.

The plunger is biased back to its retracted position by the elastic sock 14 which also provide additional functions. Elastic sock 14 is made of a rubbery elastic material having an excellent memory. The elastic sock has a circular base portion 39 and an extending tubular wall portion 40. The elastic sock, when in the rest position, adopts the configuration illustrated in FIG. 1. The base portion is made of a stretchable and elastic material. The base portion has a peripheral edge 41 that is thickened with respect to the thickness of the base portion immediately next to the peripheral edge.

FIG. 2 illustrates attachment of the sock to the apparatus and shows how the thickened peripheral edge 41 is trapped between wall 27 of base part 18 and the inner wall of top part 17. The area of the base part between the peripheral edge and the tubular wall portion 40 is quite elastic and can stretch. Peripheral edge 41 also functions to seal the fluid pathway in the apparatus. The outer end of tubular wall portion 40 is provided with an annular sealing lip 45 that fits within an annular recess 46 formed in base part 18 (see FIG. 2).

The plunger 12 has an engagement means 15 that comprises an annular shoulder extending from the base of nose portion 13. The annular shoulder sits behind base portion 39, this being best illustrated in FIG. 2. Thus, when the plunger 12 is pushed forwardly from the position illustrated in FIG. 2 to the position illustrated in FIG. 3, the engagement means 15 will push base portion 39 forwardly. As the peripheral edge 41 is trapped in place, the base portion will begin to stretch this being best illustrated in FIG. 3. As this occurs, a chamber 16 (called the variable volume chamber) opens up from a very small or zero volume best illustrated in FIG. 2, to a larger volume best illustrated in FIGS. 3 and 4. This chamber 16 forms part of the fluid flow pathway that means that fluid fills or can at least partially fill chamber 16. Of course, upon removal of the syringe tip (which pushes the plunger forwardly) from the apparatus, the plunger is pulled back into the retracted position by virtue of the stretched base portion 39 shrinking back to its rest position. This action reduces the volume of chamber 16 and causes any fluid in the chamber to be "pumped" or squeezed through flow passageway 30 and through outlet 11.

The sock is designed such that when the plunger 12 is in the retracted closed position, there is still some tension in the sock to keep the plunger in the retracted position.

The tubular wall portion 40 of the sock has an array of spaced circumferential grooves 43 which are best illustrated in FIG. 1 and FIG. 2. These grooves facilitate a control buckling of the tubular wall portion 40 from a substantially unbuckled position illustrated in FIG. 2, to a buckled position illustrated in FIG. 3. The buckling compensates for the stretching of base portion 39. The tubular wall portion (also called the sock stem) has a natural position and memory to retain the position illustrated in FIG. 2. Thus, when the wall portion adopts the buckled position illustrated in FIG. 3, it also assists in pushing back to the plunger as soon as the syringe (or other type of device) is removed from inlet 10.

Referring to FIG. 4, when the plunger 12 is in the fully open position, the plunger nose seals against annular sealing lip 45.

Figure 5:
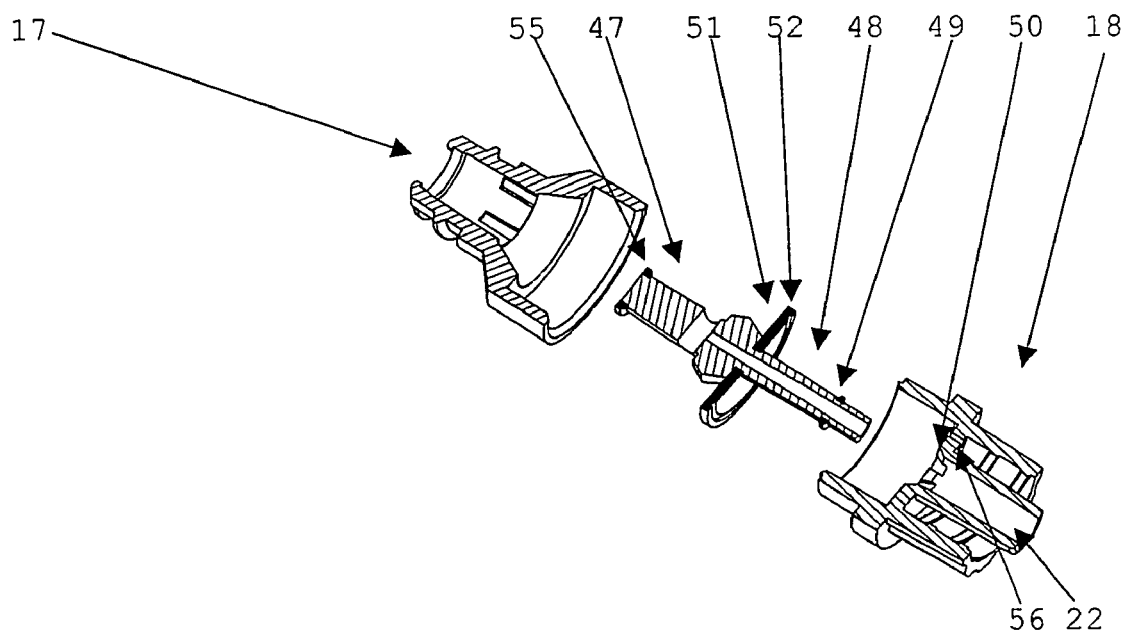
FIG. 5. Illustrates a second embodiment of the invention having a slightly different sock arrangement that does not contain a tubular portion.
Figure 6:
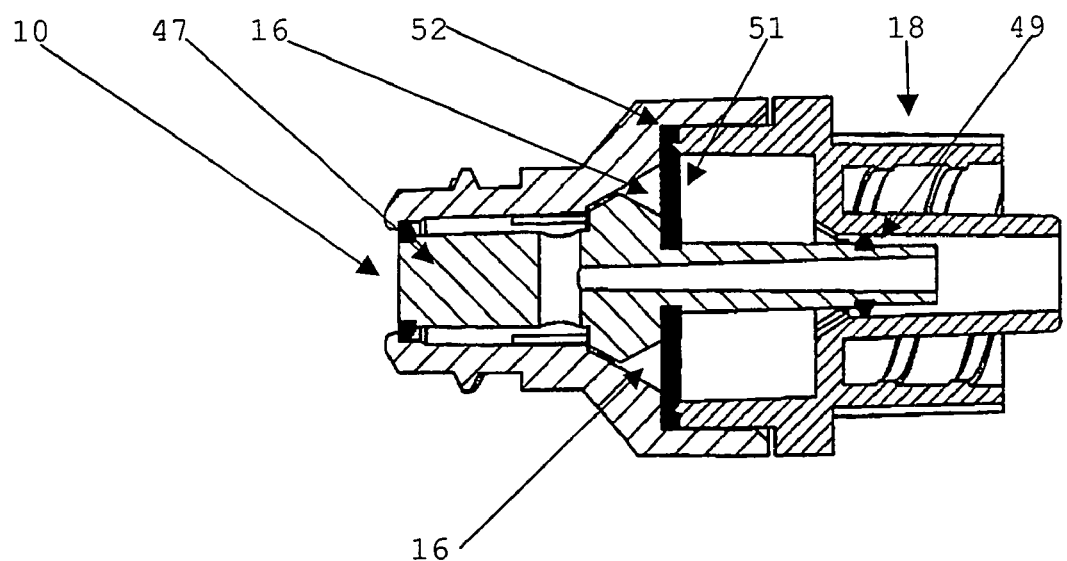
FIG. 6. Illustrates the valve assembly of FIG. 5 with the plunger in the retracted closed position and the sock in a substantially unstretched mode.
Figure 7:
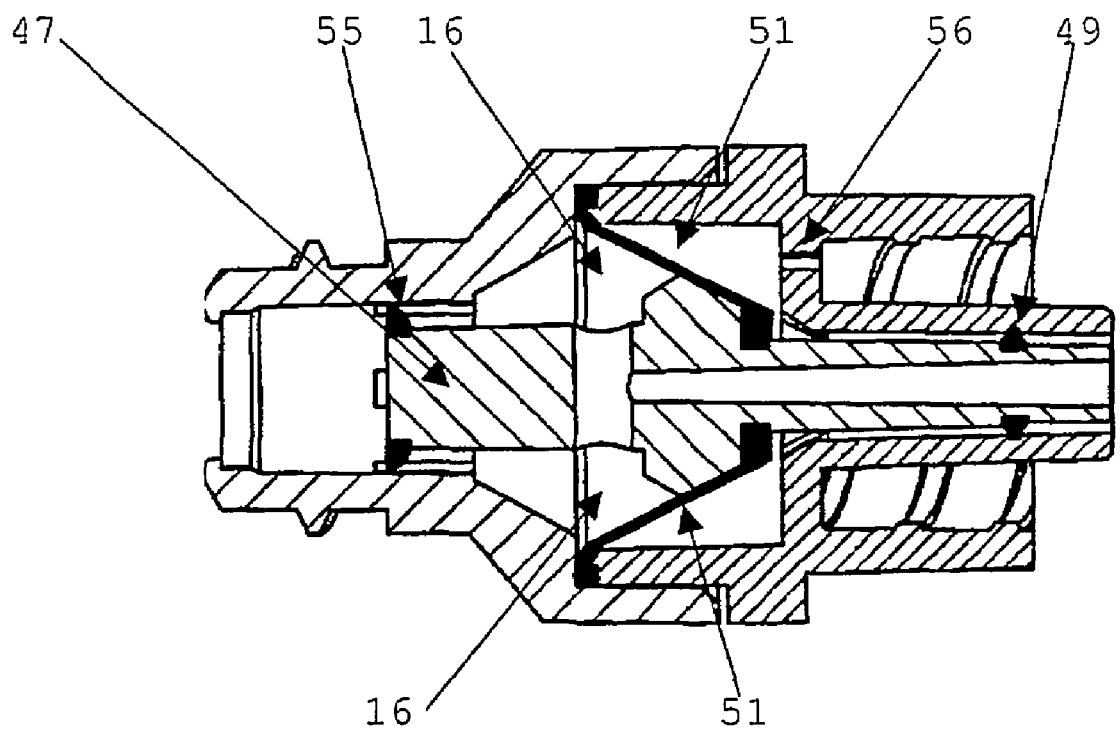
FIG. 7. Illustrates the valve assembly of FIG. 6 with the plunger has been pushed into the forward open position and the elastic sock is stretched.

FIGS. 5–7 illustrate another embodiment of the invention, the primary difference being the configuration of the elastic sock on the plunger. Like parts have been given like numbers.

In this embodiment, plunger 47 is substantially similar to the plunger described above except that the nose portion 48 contains a O ring seal 49 which is in sliding engagement with the inside wall of outer passageway 22 thereby preventing fluid from flowing along the outside wall of the nose portion 48. The plunger supports an elastic sock 51 that is disklike in configuration, and differs from the elastic sock described above in that there is no tubular portion. The sock 51 again has an outer peripheral thickened sealing edge 52 that is trapped in the valve housing as illustrated in FIG. 6 and FIG. 7.

As plunger 47 moves from its retracted position illustrated in FIG. 6 to the extended position illustrated in FIG. 7, the movement causes the elastic sock 51 to stretch. This stretching action increases the volume of the variable volume chamber 16. When the syringe tip (not illustrated) or other similar device is removed from inlet 10, plunger 47 will then be retracted back to the closed position illustrated in FIG. 6 by virtue of the bias provided by the stretched sock. Additionally, shrinking of the sock back to its initial position will reduce the volume of chamber 16 that provides the positive pressure to prevent backflow. A further O ring 55 is positioned on the outer edge of plunger 47.

In each embodiment, a small air passageway 56 is provided to allow air to pass into chamber 23 upon shrinking of the sock and to allow air to pass out of chamber 23 upon stretching of the sock.

The valve assembly prevents back flow of fluids by maintaining a positive pressure in chamber 16.

Figure 8:
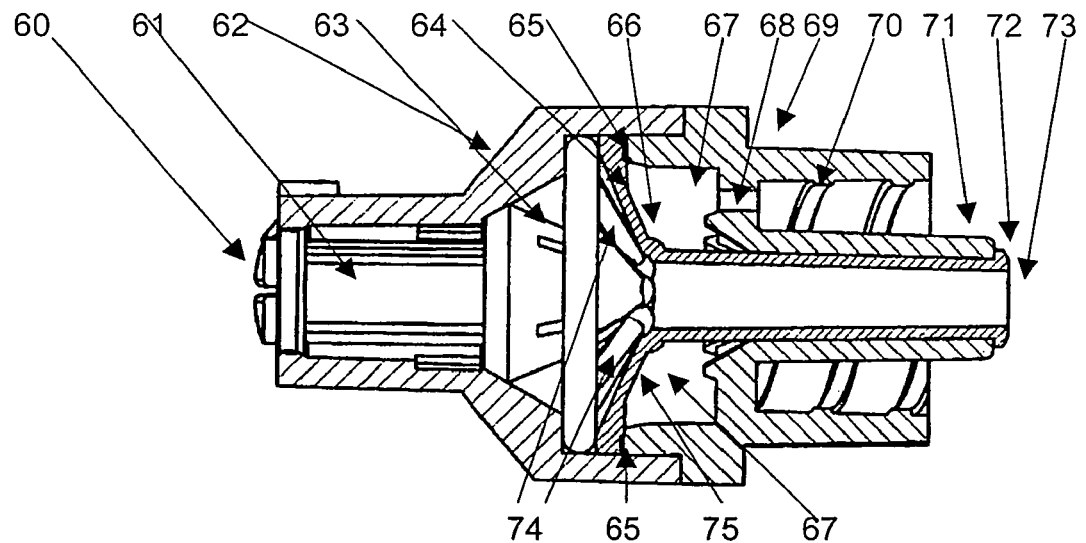
FIG. 8. Illustrates a third embodiment of the invention with the plunger in the closed position.
Figure 9:
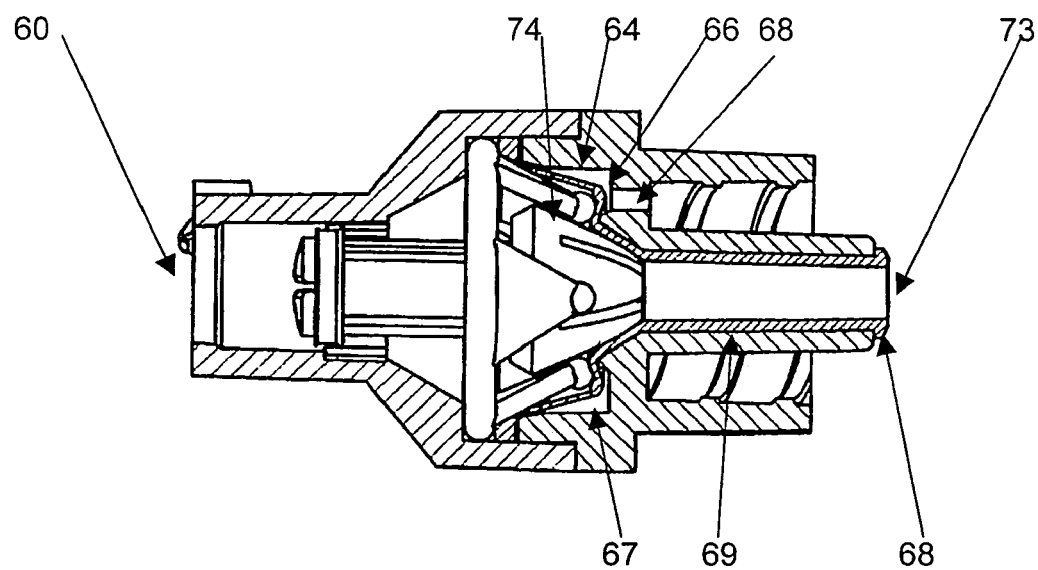
FIG. 9. Illustrates the invention of FIG. 8 in the open position.

Referring to FIGS. 8 and 9 there is illustrated an anti-siphon means that can be fitted to a valve assembly which is described in Australian patent 736326 the specification of which is incorporated herein by cross reference. In this embodiment, the anti-siphon means includes a sleeve 64 which fits generally in a bottom casing 69 which is one part of a two part housing. Sleeve 64 can be formed from an elastic material or a material that is elastic in the region where the sleeve contacts opening fingers 74. Suitably, the sleeve is formed from SANTOPRENE or similar material. Sleeve 64 has an inner portion which is dish shaped 75 and an outer portion 69 which is in the shape of a tube and which extends along the inside wall of spigot 71, and terminates in a small lip 72 which extends over the front end of spigot 71 to hold the sleeve in place. Inner portion 75 of the sleeve is sealed to the innermost annular land portion 65 of bottom casing 69. Thus, the sleeve can be positioned in bottom casing 69 prior to bottom casing 69 being attached to top casing 62. A small annular thickened portion 66 is provided on the sleeve where the dish shaped portion 75 joins or becomes part of the outer portion 69. Suitably, the entire sleeve is formed from a single piece of material.

The sleeve is designed to naturally adopt a position illustrated in FIG. 8 where it abuts against, or is closely spaced from fingers 74. In this position, the sleeve isolates the fluid pathway from the remainder of chamber 67. When valve member 61 is pushed forwardly, the arrangement adopts the position illustrated in FIG. 9. As valve member is pushed forwardly, it deforms or pushes apart fingers 74. Fingers 74 in turn push back/stretch sleeve 64 into chamber 67. This action causes air in chamber 67 to be vented from the chamber through a small vent opening 68. Vent 68 in the particular embodiment illustrated in FIG. 8 and FIG. 9 extends between chamber 67 and outlet 73. Specifically, vent 68 passes between chamber 67 and the threads 70 in the internal passageway. An advantage in having the vent in this position is that it cannot be clogged by any cleaning/wiping of the exterior of the valve assembly. Of course, it is possible for vent 68 to vent air from chamber 67 to any convenient outer part of the valve assembly.

When valve member [plunger] 61 is pushed forwardly, fluid can now pass from inlet 60 through outlet 73. When valve member 61 is pushed back from the position illustrated in FIG. 9 to the position illustrated in FIG. 8, the stretched sleeve 64 will shrink back to the position illustrated in FIG. 8, and will stay abutting against or closely spaced from the fingers 74/valve member 61. As this occurs, air will pass through vent 68 and into chamber 67 to equalise the pressure. Thus, air will pass through vent 76 and not through outlet 16. The effect of this is that as valve member 61 is retracted, fluid will not suck back through outlet 73 as air will move preferentially into chamber 67 through vent 68. The reason for this is that outlet 73 will usually be connected to some form of needle assembly or body access means and it is much more difficult to suck fluid back through outlet 73 then to have air passing through vent 68. Thus, the arrangement functions as an anti-siphon means to prevent body fluid (for instance blood) from being sucked back into the valve assembly.

Another advantage with the arrangement is that possibly contaminated air is kept separate from the fluid flow pathway of the valve assembly by virtue of the sleeve 64.

It should be appreciated that various other changes and modifications can be made to the invention without departing from the spirit and scope of the invention.

What is claimed is:

1. A valve assembly that comprises an inlet and an outlet, a flow pathway that extends through the valve assembly from the inlet to the outlet, a plunger that is positioned in the flow pathway and which can move between a forward open position where fluid can flow from the inlet to the outlet, and a retracted closed position where fluid is prevented from flowing from the inlet to the outlet, the plunger having a fluid flow pathway extending at least partially therethrough or therealong, the plunger having a forward portion, an at least partially elastic sock that has an outer end fixed to the valve assembly, and an inner portion which engages with the plunger such that reciprocation of the plunger from the retracted position to the forward position causes at least part of the sock to stretch, and a variable volume chamber having walls defined by the plunger and the sock, the chamber forming part of the flow pathway, the chamber having smaller or nil volume when the plunger is in the retracted position, and a larger volume when the plunger is in the extended position, whereby upon retraction of the plunger, the variable volume chamber reduces in volume which results in a pumping action to pump fluid through the fluid pathway towards the outlet, thereby reducing or preventing backflow.

2. The assembly of claim 1, wherein the valve assembly has an outer body formed in two parts that are attached together.

3. The assembly of claim 2, wherein one of the two parts comprises a top part having an outer passageway of smaller diameter or cross-section, and an inner passageway of larger diameter or cross-section, the inner passageway forming part of an internal chamber.

4. The assembly of claim 3, wherein the outer passageway contains at least one longitudinal slot or recess that comprise fluid ports.

5. The assembly of claim 3, wherein the other of the two parts comprises a base part which has an outer passageway of smaller diameter or cross-section, and an inner passageway of larger cross-section or diameter and which forms part of the internal chamber that is also defined by the top part.

6. The assembly of claim 5 that has a fluid flow pathway that extends through the valve assembly from the inlet to the outlet, and through the central internal chamber.

7. The assembly of claim 1, wherein the plunger has an engagement means to engage with the elastic sock.

8. The assembly of claim 7, wherein the engagement comprises an annular step or shoulder portion on the plunger and which catches against or engages with the elastic sock upon forward movement of the plunger.

9. The assembly of claim 1, wherein the sock has a substantially circular base portion, and an extending tubular wall portion.

10. The assembly of claim 9, wherein the wall portion extends substantially about the forward portion of the plunger.

11. The assembly of claim 10, wherein the base portion has a peripheral edge that is held against movement in the valve assembly.

12. The assembly of claim 11, wherein the tubular wall portion is compressible or is otherwise configured to allow it to be shortened in length, for instance by allowing the wall portion to buckle in a controlled manner.

13. The assembly of claim 1, wherein the sock has a substantial disklike configuration.

14. The assembly of claim 13, wherein the sock has an outer peripheral edge that is attached to the valve and an internal opening which is typically a central opening and through which the forward part of the plunger can pass.

* * * * *